United States Patent [19]

Grosso

[11] Patent Number: 5,759,799
[45] Date of Patent: Jun. 2, 1998

[54] MARKER FOR REVEALING CONTAMINANTS AND APPLICATION METHOD FOR PERFORMING AN ANTIBIOGRAM CARRIED OUT DIRECTLY ON A SAMPLE

[75] Inventor: Marie-Helene Grosso, Sanary, France

[73] Assignee: Bio Veto Test (S.A.R.L.), Hyeres, France

[21] Appl. No.: 725,708

[22] Filed: Oct. 4, 1996

[51] Int. Cl.⁶ ............................ C12Q 1/22; C12Q 1/18; C12Q 1/00; C12N 1/00

[52] U.S. Cl. .................... 435/31; 435/32; 435/29; 435/34; 435/4; 435/36; 435/12; 435/882; 435/883; 435/884; 435/260

[58] Field of Search ............................ 435/31, 32, 4, 435/29, 34, 36, 12, 882, 883, 884, 260; 436/63; 422/82.05, 82.09

[56] References Cited

U.S. PATENT DOCUMENTS 5,071,749  12/1991  Kondo et al. .................. 530/317

FOREIGN PATENT DOCUMENTS

| 0005891 | 12/1979 | European Pat. Off. . |
| 0075215 | 3/1983 | European Pat. Off. . |
| 0149383 | 7/1985 | European Pat. Off. . |
| 0285792 | 10/1988 | European Pat. Off. . |
| 0322591 | 5/1989 | European Pat. Off. . |
| 0322591 | 7/1989 | European Pat. Off. . |
| 0611001 | 8/1994 | European Pat. Off. . |

OTHER PUBLICATIONS

"ECCLS Standard for Antimicrobial Susceptibility Testing Diffusion Methods" ECCLS, 1985, 5:4.

28th report in the series of technical reports N. 610, WHO Geneva, 1977, 106–138 by the WHO Committee of Experts in Biological Standardization.

"New Approaches to the Study of Susceptibility of Bacteria to Antibiotics" (English language translation of Nouvelles approaches de l'étude de sensibilité des bactéries aux antibiotiques), by J.P. Flandrois, G. Carret, in the Revue Francaise du Laboratiore, vol. 151, 1986.

Libehal et al, "Preliminary Observations on the in Vitro sensitivity of Mycoplasma and Acholeplasma strains of bovine onigen," Rev. Microbiol. 1991, 22, 55–59.

Primary Examiner—Louise Leary
Attorney, Agent, or Firm—Greenblum & Berstein P.L.C.

[57] ABSTRACT

An incubation limit marker for revealing the growth of contaminants present in a sample includes at least one strain or category of classically contaminant bacteria in dehydrated form which, once regenerated, will be present at a maximum concentration of $10^3$ CFU/ml. The incubation limit marker also includes a medium used for the dehydration of the contaminant bacterium or bacteria which includes a substrate capable of being degraded by the bacterium or bacteria. The incubation limit marker further includes an indicator of the growth of the bacterium or bacteria, for example, constituted by a colored indicator of changes in pH. A process for the "in vitro" detection of the susceptibility of pathogenic bacteria to various antibiotics present in MIC (i.e., Minimal Inhibitory Concentration) in culture or antibiogram media is carried out directly from the sample of the infected medium, in the presence of the above marker, used as a signal which limits the reading time of the antibiogram.

26 Claims, No Drawings

MARKER FOR REVEALING CONTAMINANTS AND APPLICATION METHOD FOR PERFORMING AN ANTIBIOGRAM CARRIED OUT DIRECTLY ON A SAMPLE

BACKGROUND OF THE INVENTION

1. Field of the Invention

The present invention relates to a method for the "in vitro" evaluation of the susceptibility to antibiotics of germs responsible for pathology, a process currently designated by the term antibiogram.

It also relates to the marker for revealing the contaminants used in this process, which is intended to indicate the incubation limits of the antibiogram, and which is consequently called an incubation limit marker.

2. Background and Material Information

For the biologist, the choice of an appropriate antibiotic for the treatment of an infection depends, in large part:

- on the "in vitro" analysis of the susceptibility of the bacterium responsible for the infection to various antibacterial agents or antibiotics (performed by means of an antibiogram);
- on the pharmacological properties of the antibiotics (diffusion in the source of infection, toxicity, etc.); and
- on the immune state of the patient.

The role of the laboratory is to determine "in vitro" the concentrations of antibiotics necessary to inhibit or kill the bacteria. In medical practice, the selection of the antibiotics tested and the methods of investigation used will depend on the bacterial species isolated, and on the nature and the seriousness of the infectious state.

In a limited number of cases, it is possible to treat an infection without doing an antibiogram, if the epidemiological data give reason to suspect that a bacterium is probably responsible, and if little resistance to this species has developed. But in the case of severe or recidivistic infections and nosocomial infections due to bacteria which frequently have acquired resistances (staphylococci, enterobacteria, etc.), an "in vitro" evaluation of the susceptibility of the germs responsible is indispensable, as it is in numerous infections—bacteremia, meningitis, non-complicated urinary infections, for example—in which the predictive value of the antibiogram and the MIC (minimal inhibitory concentration) is necessary.

In order to define MIC, it must be recalled that the action of an antibiotic consists of hitting a molecular target represented by a precise stage in the bacterial metabolism. Globally, this results in modifications of the growth (bacteriostasis) and the survival capacity (bactericide) of the bacteria, when there is a sufficient concentration of antibiotic coming into contact with them. The determination of this concentration makes it possible to increase the susceptibility of the bacteria isolated in the clinic. Different concentrations (or limit points) define the bacteriostatic and bactericidal effects: the MIC (minimal inhibitory concentration) is the lowest concentration of antibiotic which inhibits any visible growth after an incubation time of 18 to 24 hours. It is the reference used universally to characterize the activity of an antibiotic.

By analogy with MIC, the MBC (minimal bactericidal concentration) is arbitrarily defined as the concentration of antibiotic which makes it possible to obtain, after 18 hours of contact, a survival rate less than or equal to 0.01% of the initial inoculum.

The "in vitro" activity of an antibiotic is defined by its MIC and MBC values, which can be modified by numerous factors, such as:

1) the density of the inoculum; in effect, the denser the inoculum, the more likely there are to be different kinds of bacteria, including bacteria which inactivate the antibiotic, causing differences in MIC.

2) the incubation time, temperature and atmosphere; in effect, the duration of the incubation is also a factor in the variability of MICs, which can depend on the instability of the antibiotics in solution and on the delayed "regrowth" of persistent bacteria. A reading after 16 to 18 hours of incubation at 37 degrees Celsius provides the most reproducible results.

3) The nature of the culture medium (constituent of the medium, ions, pH).

In order to mitigate this last factor influencing the "in vitro" activity of antibiotics, numerous culture media have been compared, including the Mueller-Hinton medium which constitutes the medium used universally to determine the "in vitro" activity of antibiotics.

Reproducibility of results involves a standardization of the investigation methods.

There are a plurality of standardized methods available to the biologist for evaluating the antibacterial activity of antibiotics and guiding therapeutic selection. The simplest of these remains the determination of the MIC or its approximation using an automated antibiogram method.

The methods for analyzing the MIC are also used to perform antibiograms. They are carried out according to principles of microbiology dominated by the pasteurian school and they consist:

first, of isolating in agar the bacterium responsible for the pathology in a standard culture medium in order to specifically discount contaminants that are generally present in concentrations lower than $10^3$ CFU/ml (Colony Forming Units/ml equivalent to germs/ml), which are not recognized in agar, so that only the bacteria present in concentrations greater than $10^3$ CFU/ml are analyzed;

then of testing the bacterium at a given concentration in order to perform the antibiogram in a reaction medium of the Muller-Hinton type according to the techniques currently used by the biologist, namely:

diffusion in an agar-based medium, specifically described in "ECCLS Standard for Antimicrobial Susceptibility Testing by Diffusion Methods" ECCLS, 1985, 5:4, as well as in "Report of an International Collaborative Study", Acta pathol. Microbial. Scand., Sect. B, 1971, Suppl. 217: 1–90 by H. M. Ericsson and J. C. Sherris;

or the dilution method described in the article "Nouvelles approches de l'étude de sensibilité des bactéries aux antibiotiques" in La Revue Francaise du Laboratoire, 151; 7–12.

or the automated antibiogram, which is also described in the above-mentioned document.

In summary, the method by diffusion in an agar-based medium, in order to determine the susceptibility of the bacteria to antimicrobial agents and the microbiological dosage of the antibiotics, uses the diffusion property of the antibiotic (deposit on the surface of a pre-impregnated disk of blotting paper) in an agar-based culture medium (containing a bacterium to be tested), producing a concentration gradient.

After 3 to 4 hours, it is possible to determine an inhibition zone which corresponds to the distance that the inhibiting concentration of antibiotic has had to travel before reaching a certain bacterial density.

The antibiogram by diffusion in an agar-based medium, or the disk method, is a process which is widely used because of its simplicity and its low cost. However, the quality of the results can vary as a function of several parameters which influence the constitution of the inhibition zone. Thus, for the same bacterial strain susceptible to a given antibiotic, reproducible results can only be obtained with an inoculum, a medium, and incubation conditions which are identical.

For the same antibiotic, strains of different species with different latency periods (periods of latency before the exponential growth of the bacteria) and very different generation periods but with identical susceptibility produce very different inhibition zones. That is why bacteria which vary widely from strain to strain due to their growth rates cannot be validly analyzed under the standardized diffusion test conditions, which apply to rapid-growth bacteria (enterobacteria, staphylococci, etc.) for which the critical periods vary within acceptable limits, having little influence on the inhibition zone.

On the other hand, the diffusion of the antibiotic in agar is not linear with the antibiotic concentration at the level of the source.

The preferred recommendations must be rigorously adhered to in order to guarantee the exactitude and the reproducibility of the results with this method. In France, the method used most often conforms to the standards set by the WHO (World Health Organization) presented in the 28th report in the series of technical reports N, 610, WHO Geneva, 1977, 106–138 by the WHO Committee of Experts in Biological Standardization.

The composition of the Mueller-Hinton medium is standardized, having in particular a pH of 7.4, a measured ion concentration $Mg++$ and $Ca++$ and a thymidine concentration of less than 50 ng/ml. The thickness of the agar must be 4 mm. The inoculum must be prepared, preferably from a culture agitated for 4 hours in a water bath, and adjusted by dilution to $2-3 \times 10^6$ bacteria per ml (photometric analysis). The seeding is carried out by inundation with several milliliters of this dilution.

According to the method by dilution in an agar-based medium, the antibiotic required by the treatment, as well as its MIC, is determined by seeding 1 to 5 µl of the inoculum corresponding to each bacterium tested ($10^4$ bacteria per spot) in a liquified medium at 45 degrees Celsius, each of which contains a precise antibiotic concentration.

The MIC is defined by the antibiotic concentration which leaves no colonies, or at most leaves 1 to 3 colonies, subsisting after 18 hours of incubation at 37 degrees Celsius. This is a reference method which makes it possible to simultaneously test a large number of strains (25 to 96 depending on the type of inoculator) against the same antibiotic.

The methods using dilution in a Mueller-Hinton medium are carried out in tubes (macromethod) or in microtitration plates (micromethod). Micromethods are better suited to performing antibiograms, due to the potential automation of the preparation of the antibiotic dilutions and the reading of the MICs. They allow the subsequent determination of the MBCs. However, the counting of the survivors after subculture is easier in macromethod than in micromethod (an inoculum of $10^6$ bacteria/ml represents $2 \times 106$ bacteria per 2 ml tube of medium and $5 \times 10^4$ bacteria per 50 µl cupule), which may account for a higher MBC in macromethod.

Other technical factors can influence the evaluation of the MBC, such as adhesion of the surviving bacteria to the walls of the microtitration tubes or plates, insufficient agitation before the production of the subcultures, or an antibiotic transfer phenomenon in the counting medium due to sampling an excessive aliquot of the medium (in macromethod, the volume required for subcultures must not exceed 0.1 ml; it ranges from 5 to 10 µl in micromethod).

On the other hand, there are various antibiogram methods which allow automated reading of the results, as described in the article "Nouvelles approches de l'étude de sensibilité des bactéries aux antibiotiques" by J. P. Flandrois, G. Carret, in the Revue Francaise du Laboratoire, 1986, namely:

systems using two antibiotic concentrations (eg; ABAC, API-ATB). These make it possible to classify the bacteria in categories (susceptible, intermediate, resistant) by measuring bacterial growth in the presence of two critical concentrations, high and low. Growth at both concentrations defines the resistant strains, an absence of growth defines the susceptible strains, and growth at the low critical concentration defines the "intermediate" strains. A photometric analysis of the result is carried out at the 24th hour of growth.

rapid systems (eg; AUTOBAC, COBAS-BACT, RAPID-ATB, VITEK). These analyze bacterial growth in the presence of a single antibiotic concentration (independent of the critical concentrations), chosen to make it possible at best to distinguish the populations into categories S, I, R, referring to the MIC of Lhe germs. These automated systems produce results in 3 to 6 hours.

However, recent evaluations of the various automated antibiogram systems show that concordance with the MIC reference method exists in more than 85% of cases. This percentage of concordance can vary depending on the system, and the discordances observed are specifically due to certain "bacteria-antibiotic" pairings: staphylococci in the presence of methicillin, erythromycin, and clindamycin; enterococci in the presence of cephalothin, tetracycline, and chloramphenicol; enterobacter in the presence of ampicillin, cephalothin, and tetracycline; Klebsiella in the presence of ampicillin; Serratia in the presence of polymyxines; Pseudomonas in the presence of gentamicin and amikacin. These discordances are linked to the species analyzed and to the mode of antibiotic action. Thus, the growth of microagglutinates, delayed lysis of the bacteria by certain antibiotics, subsequent regrowth, or a mechanism for inducing resistance to the antibiotic are the most frequent causes of discordances (false susceptibles and false resistants) due to the automatic reading system and to the reading period (3–6 hours or 24 hours). The difficulty of detecting certain mechanisms for resistance to β-lactams, aminosides and macrolides, due to their level or their mode of expression, also constitutes a source of errors.

All automated systems make it possible to analyze the susceptibility of single, non-exigent, rapid-growth bacteria.

As seen from the description of the three above-mentioned techniques, the antibiogram by diffusion in an agar-based medium, the dilution method, and the automated antibiogram, it is clear that each of them requires, for its implementation, strict observance of a protocol (temperature, incubation time, etc.) and cannot be generalized to any type of bacteria.

In addition to the above-mentioned drawbacks inherent in each of the systems described above, the conventional antibiogram performed according to any of these techniques principally has the following three major drawbacks stemming from the fact that they do not take into account:

the specific pharmacology of each antibiotic;

the immune state of the patient in the infection stage and/or in the presence of foreign bodies;

plurimicrobial infections; resulting in discordances between the "in vitro" tests (the results of the antibiogram) and the response to the treatment.

The first drawback is due to the utilization of a Mueller-Hinton type reaction medium, which completely ignores the effect of the environmental cultural context on the antibiotherapy. It is known that the affinity of a germ for a particular humor or tissue is not the same from one humor to the next, and that bacterial adhesiveness, and therefore pathogenic power, varies as a function of numerous factors. Faced with this multitude of anatomical sites of different natures (urine, LCR, blood, mucus, etc.), in which bacterial growth varies, the current antibiogram has only one polyvalent medium for the expression of susceptibility: the Mueller-Hinton medium. This medium, which is different from the cultural conditions of the germ causing the infection at a determined site, does not take into account the real activity of the antibiotic at the site where the infection has occurred. That is why a urinary antibiotic must be analyzed in a urinary medium (effects of pH, effects of NaCl, effects of ions, etc).

Some pharmacologists have shown that Pseudomonas, in the presence of quinolones, shows MICs varying from 1 to 100 depending on whether a Mueller-Hinton medium or a urine-based medium is used.

The second drawback mentioned above is due to the fact that the bacterium, after having been isolated, is tested at a predetermined arbitrary concentration. It is known that the concentration of the germ responsible can vary depending on the site of the infection, the immune state of the patient, and on the stage of the infection.

Thus, in terms of germ/ml (in the case of hemocultures in typhoid fevers) the germs can reach $10^4$ germs/ml in prostatitis, $10^6$ in urinary infections and $10^8$ in deep pus or purulent meningitis. Of course, as has already been pointed out, the result of the antibiogram depends on this inoculum effect.

The third drawback mentioned above results from the isolation of the pathogenic bacterium from the sample in order to perform the antibiogram. Because of this, no allowance is made for the presence of several bacteria at the same infection site, which can result in interactions, some of which are well known, namely:

1) Synergy between different germs (example of certain ecosystems):
   fusospirillary association in Vincent's angina (presence of Fusobacterium nucleatum and spirochetes)
   mycoplasmata and anaerobia in vaginoses (by pH effect)
2) Antagonism:
   Saccharomyces cerevisiae and Clostridium difficile (by competition)
   Proteus mirabilis and Streptococcus faecalis (by pH effect).

Using the standard antibiogram methods, the "in vitro" analysis of the susceptibility to antibiotics of germs in a plurimicrobial infection is then necessarily different from the "in vivo" reality, since the germs are tested in isolation in several pure colonies.

In other words, the analysis of the susceptibility to antibiotics of germs in a plurimicrobial infection will be necessarily different if the germs are analyzed simultaneously in the same medium (antibiogram performed directly on the scraping) than if the germs are tested in isolation in several pure colonies (conventional antibiogram) For these reasons, it is obviously preferable to perform an analysis of the susceptibility to antibiotics directly from the scraping, in a medium which could show, for a given antibiotic, the synergy or the antagonism of the different bacteria present in the plurmicrobial sample.

Despite this evidence, however, no reliable technique exists for performing an antibiogram directly on the sample.

Moreover, the interpretative reading of the conventional antibiogram also affects the chances of therapeutic success. It is necessary Lo know how to "read between the lines" of an antibiogram to detect a resistance mechanism which is only faintly discernible "in vitro", but which is coded into the bacterial DNA and can cause an adverse response to the treatment. This requires rigorous knowledge of these mechanisms and of the phenotypes they cause. This knowledge must not remain the prerogative of a few specialists, and it is probable that in the near future, the development of expert systems will contribute to improved validation of antibiogram techniques.

SUMMARY OF THE INVENTION

One object of the invention, therefore, is to eliminate the drawbacks of the standard or conventional antibiograms by testing for the growth (which appears as a cloudy zone) or the absence of growth of pathogenic bacteria sampled directly from the infected medium to be treated and inoculated into media which each contain a different antibiotic present in a concentration equal to its MIC.

In the process according to the invention, this object is achieved due to the fact that the evaluation of the susceptibility of the sample to various antibiotics (or antibiogram) is carried out in the presence of a marker for revealing contaminants, called an incubation limit marker.

This incubation limit marker comprises at least one strain or category of classically contaminant bacteria in dehydrated form which, once regenerated, will be present at a maximum concentration rate of $10^3$ CFU/ml, which incubation limit marker also comprises a medium used for the dehydration of the contaminant bacterium or bacteria comprising a substrate determined as a function of this bacterium or these bacteria and a growth indicator, preferably constituted by an indicator of changes in pH.

According to another embodiment, the substrate and the growth indicator such as, for example, the indicator of changes in pH are contained in the medium for rehydrating or regenerating the contaminant bacterium or bacteria.

The utilization of the incubation limit marker or (ILM) to perform an antibiogram carried out directly on the sample makes it possible to precisely detect the moment at which the contaminants present in this marker (generally equally present in concentrations less than or equal to $10^3$ CFU/ml in the sample) grow, creating a modification in this marker ILM (a change in a colored indicator, the appearance of cloudiness or a variation in the ATPasic activity).

At this precise moment, the reading of the antibiogram must be stopped, since the growth revealed by this reading no longer corresponds only to the growth of pathogenic bacteria, but also to that of the contaminants present in the sample, thus distorting the results of the antibiogram.

According to an advantageous characteristic of the invention, this precise moment is indicated and displayed, preferably by a change in a colored indicator acting as a sign of the growth of the contaminant bacteria.

Due to the fact that the growth of the contaminants is dependent on the temperature of the medium, the antibiogram can then be performed at various rates while the temperature is adjusted.

The antibiogram according to the invention, performed directly on the sample, offers the following advantages:

providing, and this is a major advantage, "in vitro" results which are more in keeping with the "in vivo" reality, since:

it guarantees that in the culture medium there will be cultural elements originating from the sample itself, in contrast with the conventional antibiogram carried out in a pure colony;

it takes into account the inoculum effect; in effect, the medium inoculated and tested against various antibiotics contains the concentrations and proportions of micro-organisms present in the infected site, and the response to the antibiotics is obtained under conditions comparable to those of the natural infected medium, no longer at an arbitrary concentration;

it takes into account the bacterial interactions that exist within the framework of plurimicrobial infections; the analysis of susceptibility to antibiotics directly from the sample is, in effect, carried out in a medium which can show, for a given antibiotic, the synergy or the antagonism of the various bacteria present in the plurimicrobial sample, which is not possible in a Muller-Hinton type medium, in which only the isolated bacterium is tested;

being rapid and easy to use; in effect, the steps for isolating the pathogenic bacterium are eliminated and the experimental conditions of the antibiogram are simplified (variable temperature, variable time, etc.);

being easy to read.

DETAILED DESCRIPTION OF THE PREFERRED EMBODIMENTS

The objects, characteristics and advantages mentioned above, as well as others, will become evident from the following description, in which non-limiting examples of the composition of the incubation limit marker are described along with a process for its utilization to perform an antibiogram carried out directly on the sample.

The marker for revealing contaminants or ILM is remarkable in that it comprises at least one category of classically contaminant bacteria present at a maximum concentration, for example less than or equal to $10^3$ CFU/ml, with its appropriate substrate, and a sign of the growth of the contaminants, preferably a colored indicator of changes in pH in a standard medium with a predetermined pH.

The classically contaminant bacterium can be from various categories depending on whether it is a bacterium which degrades urea (urease-positive bacterium) such as, for example Corynebacterium, *staphylococcus intermedius*, etc., and/or glucose (glucose-positive bacterium) such as, for example, *Escherichia coli, staphylococcus intermedius*, etc. A very large number of species of bacteria (around 90% of species) degrade glucose, such as the family of gram-negative and gram-positive bacilli, allowing an important choice for the classically contaminant bacterium for the incubation limit marker.

The choice of this bacterium can advantageously be guided by the type of infection from which the sample is taken, which contains contaminants which can be known.

The substrate is a function of the contaminant bacterium and can be, in particular, glucose, urea, etc.

The pH of the medium is kept acid when the substrate is urea, and alkaline when the substrate is glucose.

By way of example, the incubation limit marker containing the urease-positive bacterium: staphylococcus intermedius, also contains urea, an indicator of changes in a medium with an acid pH (5.5).

In order to allow better preservation of the contaminant bacterium, this bacterium is initially present in the incubation limit marker in dehydrated form so that, once regenerated, it will be present at a maximum concentration of $10^3$ CFU/ml.

According to a first form of implementation of the invention, the medium for rehydrating the dehydrated contaminant bacterium is a conventional culture medium at a predetermined pH (acid in the case of a urease-positive bacterium and alkaline in the case of a glucose-positive bacterium) and it contains:

the substrate and/or the pH change indicator.

Advantageously, it is possible to add to this rehydration medium various reagents which improve the growth of gram-positive cocci (such as staphylococci), which have a slower growth rate than gram-negative bacilli in a conventional medium.

According to another form of implementation of the invention, the substrate, the pH indicator and the reagents are contained in the dehydration medium, which corresponds to a conventional culture medium at a predetermined pH (acid in the case of a urease-positive bacterium and alkaline in the case of a glucose-positive bacterium) containing known essential elements for the stability of the dehydrated bacteria, for example: gelatin at 1% final, colt serum at 68% final, polyol at 1.2% final. On the other hand, various reagents which improve the growth of gram-positive cocci, such as staphylococci, are added to this dehydration medium. The following reagents can also be added to the rehydration medium: Arg at 0.05% final, Cys at 0.05% final, thiamine 0.1% final, niacin 0.1% final. The purpose of these additional reagents is to improve the growth of gram-positive cocci, which have a slower growth rate than gram-negative bacilli in a conventional medium.

The medium defined for this test therefore includes the elements essential to the growth of gram-negative bacilli and gram-positive cocci, and does not favor any micro-organism in either group more than another.

This medium is also suitable for the growth of the contaminants encountered in external infections: otitis, pyodermatitis.

In effect, the above-mentioned substrate, pH change indicator and reagents can be present in the dehydration medium or in the rehydration medium interchangeably, as indicated above.

The principle used in the incubation limit marker consists of revealing the growth of contaminant bacteria through the resulting changes in the pH of the medium.

In effect, the growth of a urease-positive bacterium, for example, requires the degradation of urea, which causes an alkalinization of the medium. The alkalinization of the medium during degradation of the urea is due to the release of ammonia in the following reaction:

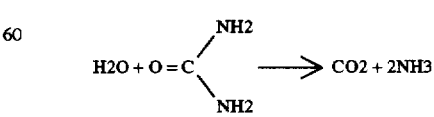

Whereas the growth of a glucose-positive bacterium, due to the degradation of glucose, causes an acidification of the medium.

Preferably, the pH indicator is phenol red, which is red at an alkaline pH and yellow at an acid pH.

According to an important characteristic of the invention, the change in the incubation limit marker occurs with kinetics which are:
- proportional to the initial concentration of contaminant bacteria; and
- proportional to the ambient temperature from 24 hours at 40 degrees Celsius to 4 days at 20 degrees Celsius.

According to the invention, the concentration of contaminant bacteria is constant, $10^3$ CFU/ml, so that the change depends solely on the ambient temperature. In effect, the heat supplied to the incubation limit marker stimulates the biochemical reactions which cause the degradation of the substrate by the contaminant bacterium. The change in pH and its revelation by the colored indicator consequently occurs more or less rapidly depending on the temperature brought to bear on the incubation limit marker.

The trials and experimentations which resulted in the present invention essentially related to the utilization of this contaminant-revealing marker to perform an antibiogram carried out directly on the sample.

However, no limitation of the application is implied.

In effect, this incubation limit marker, by virtue of its composition and its utilization, makes it possible to reveal all contaminants and can be used more generally within the scope of experiments and tests carried out directly on every sample of tissue or infectious media, in order to determine and indicate the growth of the contaminants which can be present in the sample.

In particular, this incubation limit marker can also be used within the scope of the identification of bacteria in suprapaLhological proportions (greater than $10^3$ CfU/ml) carried out directly on the sample. These bacteria are detected by their growth, which clouds the medium before or at the same time the incubation limit marker changes.

According to the invention, the performing of an antibiogram consists, first of all, of sampling the infected medium containing the pathogenic bacteria to be tested, in the form of a scraping of the infected tissue or in the form of biological liquids (infected extravasation fluid, etc.), and then inoculating it into culture media containing different antibiotics at their MIC. Preferably, the sampled medium is diluted to $10^2$ CFU/ml in a transport medium which keeps all the species of bacteria viable in the same concentrations as in the sample, then seeded in a culture medium, and this culture medium seeded with the various antibiotics present is then inoculated at their MIC.

By way of example, in this particular analysis, 200 µl of this medium was distributed in various wells or other receptacles containing different antibiotics at their MIC, in a conventional culture medium.

Due to the transport medium used, which keeps the seeded transport medium stable for 10 hours at the ambient temperature and for 24 hours at 4–8 degrees Celsius, the laboratory technician, or more generally the handler, is not required to inoculate soon after seeding.

In order for the results of the antibiogram to be correct, it is necessary for the incubation limit marker to be rehydrated or prepared when the sample is inoculated with different concentrations of antibiotics. This moment determines the starting point (T=0) of the various reactions occurring between the bacteria, antibiotics, contaminants and substrates of the sample present in the different wells or receptacles containing the various antibiotics as well as the reaction of the degradation of the substrate by the contaminant bacteria in the incubation limit marker.

The reading of this antibiogram is simple in that it is merely necessary to determine, before or at the same time as the change in the color of the incubation limit marker, the well or receptacle in which no bacterium has developed (no clouding) in order to know which antibiotic(s) is or are required for the treatment of the infection for which the sampling has been performed.

This reading is based on the color change in the incubation limit marker.

For example, the reading of the antibiogram is stopped as soon as the incubation limit marker, which is initially yellow (pH 5.5) turns red, when the incubation limit marker contains the urease-positive bacterium, staphylococcus intermedius, urea and phenol red.

According to one advantageous characteristic of the invention, the change in the incubation limit marker is proportional to the surrounding temperature, requiring from 18 to 24 hours at 40 degrees Celsius, from 36 to 44 hours at 25 degrees Celsius and 4 days at 20 degrees Celsius.

Thus it is possible to perform an antibiogram directly on the sample at temperatures which can vary from one test to the next or which can vary over time for a constant temperature. in effect, as long as the incubation limit marker does not change, it is possible to read the antibiogram without risking interference from contaminants. The effect of the temperature on the growth of the bacteria will occur in the incubation limit marker as well as in the antibiogram system in which the germs responsible for the infection are located.

No matter what the temperature, the pathogenic bacteria present at the site of the infection grow before the incubation limit marker changes. Only the time that it takes the incubation limit marker to change depends on the ambient temperature, generally:
- 40 degrees Celsius—18 to 24 hours
- 25 degrees Celsius—36 to 44 hours
- 20 degrees Celsius—4 days (96 hours).

This safety not only allows antibiograms to be performed directly from the sample but makes it possible not to worry about temperature conditions, thereby allowing these tests to be performed in ambulatory situations, either by veterinarians, or by doctors who are away from a laboratory unit. In effect, it is possible to perform the antibiogram without an incubator and without temperature regulation.

Under simplified operating conditions (from the sample, without concern for the temperature) , this antibiogram can be performed not only by non-specialized personnel, but also by the patient himself (within the scope of urinary infections in pregnant women far removed from a medical center, war-inflicted wounds, etc.), and therefore within the scope of humanitarian medicine or war medicine.

Thus, the veterinarian or other user of this antibiogram can be certain that the antibiotic revealed by this antibiogram to be effective "in vitro" will also produce a therapeutic result. Taking into account the preceding disclosure, the means to allow antibiograms according to the invention to be performed can advantageously be produced in the form of kits.

In addition to the knowledge of the type or types of antibiotics required for treatment, the antibiogram carried out according to the invention also makes it possible to know whether or not the proportion of the bacterium sampled and tested is suprapathological (in which case the germ is probably endowed with pathological power), no matter what the temperature at which the antibiogram is carried out.

In effect, if bacterial growth occurs in the tubes containing a specific antibiotic at its MIC concentration and a sample (indicated in the form of cloudiness) before or at the same time the incubation limit marker turns from yellow to red, it is certain that the bacterium present at the infection site is present at a concentration higher than $10^3$ CFU/ml, and therefore corresponds to a so-called suprapathological proportion (in which case the germ is probably endowed with pathological power).

Conversely, if no bacterial growth occurs before or at the same time the incubation limit marker changes, this indicates that no bacterium is present at the infection site in concentrations higher than $10^3$ CFU/ml.

If bacterial growth occurs after the incubation limit marker has turned red, this can indicate:

a contaminant if the sample is an external sample (mucus, pus, urine, etc.);

a germ in a deep humor at a rate higher than $10^3$ CFU/ml (example: hemoculture or LCR: medium not containing any contaminant).

The instant application is based upon French Patent Application No. 95.04421, filed on Apr. 6,1995, the disclosure of which is hereby expressly incorporated by reference thereto in its entirety.

What is claimed is:

1. Incubation limit marker for revealing growth of contaminants present in a sample after the incubation limit marker has been rehydrated or prepared, comprising:

at least one strain or category of classically contaminant bacteria in dehydrated form which, once regenerated, will be present at a maximum concentration of $10^3$ CFU/ml;

a medium used for dehydration of said at least one classically contaminant bacteria which includes a substrate capable of being degraded by said at least one classically contaminant bacteria; and an indicator of the growth of said at least one classically contaminant bacteria.

2. The incubation limit marker of claim 1, wherein the indicator comprises an indicator which undergoes a change in color with changes in pH.

3. The incubation limit marker of claim 2, wherein the colored indicator is phenol red.

4. The incubation limit marker of claim 1, wherein the at least one classically contaminant bacteria is at least one member selected from the group consisting of urease-positive bacteria and glucose-positive bacteria.

5. The incubation limit marker of claim 1, wherein the incubation limit marker has a pH of 5.5, and comprises staphylococcus intermedius bacteria, urea, and phenol red.

6. The incubation limit marker of claim 1, wherein the incubation limit marker has a pH of 10, and comprises glucose-positive bacteria, glucose, and phenol red.

7. The incubation limit marker of claim 1, wherein the medium comprises reagents which improve the growth of gram-positive cocci.

8. Incubation limit marker for revealing growth of contaminants present in a sample after the incubation limit marker has been rehydrated or prepared, comprising:

at least one strain or category of classically contaminant bacteria in dehydrated form which, once regenerated, will be present at a maximum concentration of $10^3$ CFU/ml;

a medium for rehydration or regeneration of said at least one classically contaminant bacteria, which includes a substrate capable of being degraded by said at least one classically contaminant bacteria; and an indicator of the growth of said at least one classically contaminant bacteria.

9. The incubation limit marker of claim 8, wherein the indicator comprises an indicator which undergoes a change in color with changes in pH.

10. The incubation limit marker of claim 9, wherein the indicator is phenol red.

11. The incubation limit marker of claim 8, wherein the at least one classically contaminant bacteria is at least one member selected from the group consisting of urease-positive bacteria and glucose-positive bacteria.

12. The incubation limit marker of claim 8, wherein the incubation limit marker has a pH of 5.5, and comprises bacteriastaphylococcus intermedius bacteria, urea, and phenol red.

13. The incubation limit marker of claim 8, wherein the incubation limit marker has a pH of 10, and comprises glucose-positive bacteria, glucose, and phenol red.

14. The incubation limit marker of claim 8, wherein the medium comprises reagents which improve the growth of gram-positive cocci.

15. Method for "in vitro" detection of susceptibility of pathogenic bacteria directly from a sample to various antibiotics present at Minimal Inhibitory Concentration in an antibiogram medium, comprising:

combining at least one antibiotic present at Minimal Inhibitory Concentration and a sample of infected medium to form an antibiogram medium;

preparing an incubation limit marker comprising:

at least one strain or category of classically contaminant bacteria in dehydrated form which, once regenerated, will be present at a maximum concentration of $10^3$ CFU/ml, a medium used for dehydration of said at least one classically contaminant bacteria which includes a substrate determined as a function of said at least one classically contaminant bacteria, and an indicator of growth of said at least one classically contaminant bacteria; and determining effectiveness of the at least one antibiotic by determining whether the antibiogram medium turns cloudy before or at the same time the incubation limit marker changes color, wherein said incubation limit marker is used as a signal which limits reading time of the antibiogram medium.

16. The method of claim 15, wherein the method is carried out at a temperature between 20 and 40 degrees Celsius and for a time between 18 hours and 4 days.

17. The method of claim 15, wherein the incubation limit marker is rehydrated at the moment the sample is combined with the at least one antibiotic.

18. The method of claim 15, wherein prior to combining the sample and the at least one antibiotic, the sample is diluted in a transport medium which keeps pathogenic bacteria present in the sample viable.

19. The method of claim 18, wherein the sample is diluted to $10^2$ CFU/ml, then 200 µl of the diluted sample is combined with the at least one antibiotic.

20. The method of claim 15, wherein cloudiness of the antibiogram medium before the color change of the incubation limit marker indicates a suprapathological quantity of bacteria in the sample.

21. Method for "in vitro" detection of susceptibility of pathogenic bacteria directly from a sample to various antibiotics present at Minimal Inhibitory Concentration in an antibiogram medium, comprising:

combining at least one antibiotic present at Minimal Inhibitory Concentration and a sample of infected medium to form an antibiogram medium;

preparing an incubation limit marker comprising:

at least one strain or category of classically contaminant bacteria in dehydrated form which, once regenerated, will be present at a maximum concentration of $10^3$ CFU/ml, a medium used for rehydration or regeneration of said at least one classically contaminant bacteria which includes a substrate capable of being degraded by said at least one classically contaminant bacteria, and an indicator of growth of said at least one classically contaminant bacteria; and determining effectiveness of the at least one antibiotic by determining whether the antibiogram medium turns cloudy before or at the same time the incubation limit marker changes color, wherein said incubation limit marker is used as a signal which limits reading time by changing color.

22. The method of claim 21, wherein the method is carried out at a temperature between 20 and 40 degrees Celsius and for a time between 18 hours and 4 days.

23. The method of claim 21, wherein the incubation limit marker is rehydrated at the moment the sample is combined with the at least one antibiotic.

24. The method of claim 21, wherein prior to combining the sample and the at least one antibiotic, the sample is diluted in a transport medium which keeps pathogenic bacteria present in the sample viable.

25. The method of claim 24, wherein the sample is diluted to $10^2$ CFU/ml, then 200 µl of the diluted sample is combined with the at least one antibiotic.

26. The method of claim 21, wherein cloudiness of the antibiogram medium before the color change of the incubation limit marker indicates a suprapathological quantity of bacteria in the sample.

* * * * *